United States Patent [19]

Mazur et al.

[11] Patent Number: 5,137,660
[45] Date of Patent: Aug. 11, 1992

[54] REGIOSELECTIVE SYNTHESIS OF 1,3-DISUBSTITUTED GLYCERIDES

[75] Inventors: Adam W. Mazur, Cincinnati; George D. Hiler, II, Harrison, both of Ohio

[73] Assignee: The Procter & Gamble Company, Cincinnati, Ohio

[21] Appl. No.: 670,540

[22] Filed: Mar. 15, 1991

[51] Int. Cl.$^5$ .................................. C11C 3/02
[52] U.S. Cl. .................... 536/18.2; 435/134; 435/137; 554/79; 554/82; 554/173
[58] Field of Search .............. 260/410.7; 435/134, 435/137

[56] References Cited

U.S. PATENT DOCUMENTS

| | | | |
|---|---|---|---|
| 3,989,728 | 11/1976 | Marten | 260/410.7 |
| 4,865,978 | 9/1989 | Serota | 435/134 |

FOREIGN PATENT DOCUMENTS

| | | |
|---|---|---|
| 0064855 | 4/1982 | European Pat. Off. |
| 064855 | 11/1982 | European Pat. Off. |
| 0126416 | 5/1984 | European Pat. Off. |
| 0237092 | 2/1987 | European Pat. Off. |
| 321777 | 6/1989 | European Pat. Off. |
| 61-173791 | 1/1985 | Japan |
| 6206159 | 9/1985 | Japan |
| 234590 | 10/1985 | Japan |
| 62-278988 | 5/1986 | Japan |
| 1-019042 | 1/1989 | Japan |

OTHER PUBLICATIONS

Pieroni et al, European J Biochem, "Lipases Catalyze Hydrolysis of Fatty Acid Anhydrides", vol. 193, No. 1, pp. 249–253, 1990.

Lazar, et al., World Conference on Emerging Technologies in the Fats and Oil Industry, "Synthesis of ester by lipases", pp. 346–354 (1986).

Primary Examiner—Jose G. Dees
Assistant Examiner—D. D. Cain
Attorney, Agent, or Firm—Rose Ann Dabek; Jerry J. Yetter; Richard C. Witte

[57] ABSTRACT

A process for the selective esterification of glycerol and 1-glyceryl derivatives to 1,3-disubstituted glycerides is disclosed. This process uses a water immiscible solvent, either a hydrocarbon or halogenated hydrocarbon, a 1,3-lipase and fatty acid anhydrides. This reaction mixture selectively esterifies the primary alcohol groups of glycerol or glycerol derivatives. The preferred derivatives of glycerol are alkyl ethers, alkyl phosphates, phospholipids, alkyl and diaklyl phosphates, and sugar glycosides.

18 Claims, No Drawings

5,137,660

REGIOSELECTIVE SYNTHESIS OF 1,3-DISUBSTITUTED GLYCERIDES

FIELD OF THE INVENTION

This invention relates to a lipase-catalyzed introduction of 1,3-functionality into glycerol and its derivatives. These 1,3-substituted glycerols are prepared by a synthetic route which involves regioselective esterification of glycerol or a (1)3-monoderivative with fatty acid anhydrides. This reaction can be followed by further acylation to obtain specific trisubstituted glycerol compounds.

BACKGROUND OF THE INVENTION

In the food industry, diglycerides are becoming increasingly important as low calorie fatty materials. They can also be used to make specific triglycerides. Regiospecific triglycerides are important for making cocoa butter substitutes, low calorie fats and other tailored triglycerides. Esterification of glycerol with fatty acids using both chemical and enzymic (lipases) catalysts is difficult to control and frequently mixtures of monoglycerides and diglycerides are formed. Being hydrolytic enzymes, lipases require anhydrous conditions when used as the esterification catalysts. Otherwise, the reaction equilibrium will be driven towards hydrolysis. To overcome this limitation, a large excess of the acylating reagent (acid or ester) is used and the reaction products, such as water or alcohol, are being constantly removed. Another method involves irreversible esterification with active esters. Large excesses of the acylating reagents can be thus avoided but active esters are expensive.

Regiospecific diglycerides i.e., 1,3 diglycerides, are important not only for preparing regiospecific triglycerides but, as compounds in their own right Derivatives of monoglycerides are important in the food and drug industry Such derivatives include 1-alkyl-3-acyl glycerol, 1-lysophospholipid-3-acyl glycerol, glycerol glucolipids and 1-alkoxy-3-acyl glycerols. Lysophosolipids are used in foods and cosmetics.

To date, simple synthetic methods for introducing 1,3-functionality, i.e., a sugar, phosphate, sulfate, ether, etc. on a glycerol moiety have not been known. The majority of known procedures are multi-step processes and require protecting groups to discriminate among the primary and secondary hydroxy groups of glycerol. Such multi-step processes are not easily adapted to industrial synthesis.

BACKGROUND ART

European Patent Application 126,416 (Asahi Denka Kogyo, 1984) describes a continuous transesterification of fat or oil using lipase enzymes. The lipase has 1,3-specificity and is fixed on a porous solid or Chitosan derivative as a carrier. Preferably alcohols are added during the reaction. The most preferred alcohols are aliphatic alcohols having 4-18 carbons. The preferred are butyl, hexyl, octyl and decyl alcohols. The level of alcohol is 50-90 mol % of the free fatty acid estimated to be produced. The level of water is controlled so that 1,2-diglycerides are formed. Fatty acid is then added to make triglycerides. The water activity of the reaction mixture is from 0.5 to 0.9.

Japanese 62,061,591 (assigned Kao, 1985) describes an interesterification reaction using an enzyme in the presence of water, dihydric or trihydric alcohol (glycol or glycerol). The enzyme used is obtained by adding a water-insoluble carrier to a lipase containing medium which is then dried.

Japanese 61,173,791 (assigned Kao, 1986) describes a method for non-specifically hydrolyzing oils using lipase in which the aqueous phase contained from 10% to 40% glycerol After hydrolysis an oily layer, an emulsion and an aqueous layer are formed. The emulsion layer is recovered and reused.

Japanese 62,278,988 (assigned Kao, 1987) discloses an enzymic or microbial reaction. Two phases are prepared, a non-aqueous solution and an aqueous solution The reaction occurs at the interface of these two phases.

European patent application 237,092, filed by Holmberg (assigned Berol Kemi, 1987) describes a transesterification of triglycerides which is carried out in the presence of a lipase with a hydrophobic part (organic solvent) and a surface active component in water under strictly controlled conditions. Hexane is used for the hydrophobic material. Both surfactants and auxiliary surfactants are used. Alcohols and glycol ethers are listed as surface active components, including butanol, pentanol and hexanol.

In general, the described processes require low water activity or other strictly controlled conditions. Accordingly, an economical process which produces relatively pure 1,3-substituted glycerol derivatives in high yield is desirable. It has been found that an esterification reaction of glycerol or 1(3)-monoderivative of glycerol with an acid anhydride, carried out in the presence of a hydrocarbon, methylene chloride or other chlorinated hydrocarbon and catalyzed by lipase can produce a 1,3-disubstituted derivative of glycerol in good yield.

It is an object of this invention to provide 1,3-disubstituted glycerides in high yields by a simple process.

It is another object of this invention to prepare 1,3-diglycerides which can then be esterified to produce triglycerides through the use of a normal esterification reaction using acid chlorides or acid anhydrides. This latter esterification can be carried out using enzymic or chemical catalysts.

All percentages herein are by weight unless otherwise indicated.

These and other objects of this invention will become obvious from the descriptions herein.

SUMMARY OF THE INVENTION

Described herein is a process for preparing 1,3-disubstituted glycerides by enzymic esterification comprising the steps of..

(1) mixing a catalytic amount of lipase enzyme with a water immiscible hydrocarbon or chlorinated hydrocarbon, glycerol or glycerol derivative, and a fatty acid anhydride at from about 2° C. to the boiling point of the reaction mixture for at least one hour; and (2) separating the phases and optionally recovering the 1,3-disubstituted glycerol from the organic phase.

1,2,3-Triacyl glycerides can be prepared by reacting the 1,3-disubstituted glycerides with an acid anhydride or an acid chloride under anhydrous conditions in the presence of a chemical catalyst, e.g., 4-N,N-dimethylaminopyridine or an enzymic catalyst.

DETAILED DESCRIPTION OF THE INVENTION 1,3-disubstituted glycerides prepared according to this invention generally have the formula:

$$\begin{array}{c} CH_2OR \\ | \\ CHOH \\ | \\ CH_2OR'' \end{array}$$

wherein R stands for an alkyl saturated or unsaturated fatty acid acyl group having from 1 to 22 carbons; R" can be equal to R or be an alkyl group having from 1 to 22 carbon atoms, a carbohydrate moiety, preferably glucose, fructose, sucrose or maltose, a phosphate, a phosphonate or a sulfate.

The alkyl fatty acids used herein preferably have from about 2 to about 24 carbon atoms, preferably, from 8 to 24 carbon atoms. The fatty acids can be either saturated or unsaturated. The unsaturated fatty acids can be mono-unsaturated or polyunsaturated fatty acids. The positions occupied by R and R" are the 1 and 3 positions.

A. Definitions

By "1,3-diacylglyceride" is meant a glycerol molecule esterified on the first and third carbon atoms with a medium or long chain fatty acid. The acids will be identical.

By "medium chain fatty acid," as used herein, is meant a saturated fatty acid, unsaturated fatty acid, or mixture thereof, having 6 to 12 carbon atoms.

By "medium chain fatty acid anhydride" as used herein, is meant the dehydration product of two medium chain fatty acids.

By "medium chain saturated fatty acid," as used herein, is meant $C_6$ (caproic), $C_8$ (caprylic), $C_{10}$ (capric), $C_{12}$ (lauric), or saturated fatty acids, or mixtures thereof. The $C_7$ and $C_9$ saturated fatty acids are not commonly found, but they are not excluded from the possible medium chain fatty acids.

By "long chain fatty acid," as used herein, is meant a saturated fatty acid, unsaturated fatty acid, or mixture thereof, having 14 to 24 carbon atoms.

By "long chain saturated fatty acid," as used herein, is meant $C_{14}$ (myristic) and $C_{16}$ (palmitic), $C_{18}$ (stearic), $C_{19}$ (nonadecylic), $C_{20}$ (arachidic), $C_{21}$ (heneicosanoic), $C_{22}$ (behenic), $C_{23}$ (tricosanoic), or $C_{24}$ (lignoceric) saturated fatty acids, or mixtures thereof.

By "glycerol derivative" is meant a monosubstituted glycerol, substituted at the primary alcohol (1 or 3) wherein the derivative is an alkyl ether, a carbohydrate bonded through a glycosidic linkage, a liphophosphate, or an alkyl phosphate.

By "alkyl ether" is meant an ether having the formula $R_1$—O— wherein $R_1$ is an alkyl group having from 1 to 18 carbons.

By "glycosidic sugar" or "sugar glucoside" is meant a sugar which is bonded to the glycerol molecule through the acetal or ketal linkage, i.e. the first carbon of an aldehyde sugar or the second carbon of a ketone sugar. The preferred sugar glycosides or carbohydrate glycosides are those wherein the sugar moiety is glucose, fructose, maltose, sucrose, and tri- or tetrapolysaccharides of glucose.

By "phospholipid" herein is meant a phosphate derivative of glycerol wherein the phosphate is a phosphocholine or other amino phosphate derivative, or a phosphate.

By "alkyl phosphate" is meant a phosphate derivative of glycerol wherein at least one of the hydroxyl group is substituted with an alkyl group having from 1 to 22 carbon atoms. Preferably, both of the hydroxy groups of the phosphate are substituted with alkyl groups By "1,3-disubstituted derivatives of glycerol" is meant that both of the primary alcohols of glycerol are derivatized, i.e. the 1 and 3 hydroxy groups are substituted. One of these substituents must be an acyl group formed by esterifying the corresponding glycerol derivative with the fatty acid anhydride by the process herein For example, an alkyl ether glycerol moiety is reacted with a fatty acid anhydride to make a 1-acyl-3-alkoxy glyceride.

As used herein, the term "comprising" means various components or steps can be conjointly employed in the present invention. Accordingly, the term "comprising" encompasses the more restrictive terms "consisting essentially of" and "consisting of."

ESTERIFICATION OF GLYCERINE TO 1,3-DISUBSTITUTED GLYCERIDES

The process herein is a lipase-catalyzed introduction of 1,3-functionality in glycerol and its derivatives where one of the substituents is an acyl group. These 1,3-disubstituted glycerols are prepared by a synthetic route which involves regioselective esterification of glycerol or 1(3)-monoderivatives of glycerol with fatty acid anhydrides in the presence of 1,3-specific lipase. This reaction can be followed by acylation of the remaining free hydroxy group to obtain specific trisubstituted glycerol compounds.

Esterification of glycerol to form a 1,3-disubstituted glyceride is carried out in a single phase mixture of hydrocarbon or chlorinated hydrocarbon and the starting glycerol or its derivatives, fatty acid anhydride and a 1,3-specific lipase.

Any 1,3-specific lipase can be used for the esterification. The lipases derived from the species aspergillus and rhizopus can be used Specific lipases include those derived from aspergillus oryzae, aspergillus niger, mucor javanicus, mucor miehei, pancreatic, rhizopus delamar, rhizopus japonicus. These include MAP from Amano (Japan), lipolase and lipozyme from Novo (Netherlands). The amount of enzyme used is the amount of enzyme necessary to catalyze the reaction at a reasonable rate under low water conditions. Too slow a rate will prolong the reaction time. The preferred form of the enzyme is an immobilized enzyme (lipozyme) or other form which has enhanced reactivity and stability in an organic solvent.

The enzyme concentration depends upon the amount of active protein in the enzyme preparation Enzyme can be dried, immobilized on a resin or covalently bonded to or absorbed on a support, or be in solution. The concentration needed to esterify the glycerol depends upon the form, the type and the activity of the enzyme. The amount required is a catalytic amount. A catalytic amount is enough to esterify glycerol or its derivative to a 1,3-disubstituted glyceride at a reasonable rate but not so much as to force the reaction to form triglycerides. One skilled in the art can easily determine the catalytic amount by running a small scale reaction and looking at the final products.

The requisite alkyl fatty acid anhydride is dissolved in the water insoluble hydrocarbon, methylene chloride or other chlorinated hydrocarbon. Any water immiscible hydrocarbon solvent which is essentially inert to the lipase can be used. Some solvents can denature enzymes. The glycerol or glycerol derivative must be solubilized sufficiently by the solvent so that the reaction can proceed.

Since these products can be used in foods and pharmaceuticals, a food approved or edible hydrocarbon should be used. The hydrocarbon can be an alkane with from 5 to 10 carbons, an aromatic hydrocarbon such as benzene, toluene or xylene or halogenated hydrocarbons such as chloroform, methylene chloride or carbon tetrachloride. The preferred hydrocarbon solvents are hexane, pentane, petroleum ether and isooctane The preferred chlorinated hydrocarbon is methylene chloride.

Any acid anhydride can be used to esterify the glycerol or its derivatives. Acid anhydrides of fatty acids are commercially available or can be synthesized by conventional means. The preferred fatty acids anhydrides have $C_4$ to $C_{24}$ carbons.

The long chain fatty acids per se or naturally occurring fats and oils can serve as sources of the long chain saturated fatty acids. For example, soybean oil and high erucic acid rapeseed oil hydrogenated to an I.V. of about 10 or less are good sources of stearic and behenic fatty acids, respectively. Odd chain length long chain fatty acids can be derived from certain marine oils.

The fatty acids can be derived from plants, animals or from synthetic fats or oils. Liquid oils, e.g., unsaturated vegetable oils, can also be used as precursors for the fatty acids. These acids can be partially hydrogenated to convert some of the unsaturated double bonds of the fatty acid constituents into saturated bonds.

Preferred acids are hexanoic, octanoic, decanoic, lauric, palmitic, stearic and behenic acids. Preferred unsaturated fatty acids include oleic acids. Long chain saturated fatty acids have frequently low solubility in the hydrocarbon solvent. Therefore they are not preferred for use herein.

The mole ratio of acid anhydride to glycerol or glycerol derivatives is from about 1:1 to about 3:1 anhydride to glycerol. Too large an excess of anhydride may cause formation of triglycerides instead of the 1,3-diacylglyceride or 1,3-disubstituted glyceride.

The reaction mixture has the following proportions by weight percent:

3% to 40%—glycerol or glycerol derivative
20% to 60%—hydrocarbon or chlorinated hydrocarbon
3% to 40%—fatty acid anhydride The reaction is carried out at ambient temperature or at temperatures of from about 2° C. to about 5° C. or the boiling point of the reaction mixture for from 0.5 hours to about 24 hours. The reaction is mixed using a standard laboratory mixer.

1,3-diacylglycerides can be isolated from the organic phase by crystallization or evaporation of the organic solvent. Liquid 1,3-diacylglycerides can be purified by distillation under controlled conditions since distillation frequently causes rearrangement or isomerization to 1,2-diacylglycerides.

The 1(3)-substituted-3(1)-acylglycerides can be isolated by crystallization or evaporation of the solvent. The exact method of purifying them will depend upon the properties of the glycerol derivative.

1,3-Diacylglycerides or 1(3)-substituted-3(1)-acylglycerols can be further esterified to trisubstituted glycerols by any conventional esterification reaction. Such techniques include esterification with acid chlorides or acid anhydrides under essentially anhydrous conditions (0.5% or less water). For example esterification with a fatty acid anhydrides in the presence of 0.3% to about 1% (mole weight basis) of 4-N,N-dimethylaminopyridine can be used to make stereospecific triglycerides from 1,3-diacylglycerides or 1,3-substituted acylglycerols. Catalysts which are known to induce rearrangement should be avoided as they will cause the disubstituted or trisubstituted glycerols to rearrange, thus producing a mixture of materials and not the desired specifically trisubstituted glycerols.

The purified mixture of trisubstituted glycerols can also be subjected to bleaching and deodorizing steps for color and flavor/aroma improvement using conventional techniques well known in the fats and oils art. Alternatively, the reaction mixture can be bleached using conventional bleaching earth and/or activated carbon prior to purification. In the case of trisubstituted glycerols which have unsaturated fatty acid residues or mixtures of unsaturated and saturated fatty acid residues, the triglycerides can be hydrogenated, before or after purification, to convert the unsaturated fatty acid residues to saturated fatty acid residues.

Uses of Triglycerides as Reduced Calorie Fats

Triglycerides of the type MML/MLM obtained according to the present invention (where L is a long chain saturated fatty acid residue and M is a medium chain saturated fatty acid residue) can be used as reduced calorie fats to partially or totally replace normal triglyceride fat in any fat-containing food composition comprising fat and nonfat ingredients to provide reduced calorie benefits. In order to obtain a significant reduction in calories, it is necessary that at least about 50% of the total fat in the food composition, or at least about 20% of the caloric value of the food, comprise the reduced calorie fat.

EXAMPLE I 1,3-Didecanoyl glycerol

A mixture of glycerol (54.3 mmole, 5.0 g), decanoic anhydride (108.6 mmole, 35.45 g) and immobilized Lipozyme (10.0 g) is refluxed in methylene chloride (250 ml) for 10 hours. Enzyme is separated by filtration. The solvent is evaporated, the oily residue is dissolved in hexane (500 ml) and cooled in dry ice for 15 min. The collected precipitate is recrystallized from petroleum ether (500 ml) giving 16.8 g (77%) of the product.

EXAMPLE II 1,3-Didecanoyl-2-docosanoyl glycerol

A solution of 1,3-didecanoyl glycerol (40.6 mmole, 16.25 g), docosanoic anhydride (40.6 mmole, 26.9 g) and 4-N,N-dimethylaminopyridine (DMAP) (12.2 mmole, 1.5 g) in methylene chloride (350 ml) is refluxed for 2 hours. On cooling the reaction mixture to 0° C., docosanoic acid and the remaining docosanoic anhydride precipitated and was filtered. The filtrate is evaporated and dissolved in petroleum ether (500 ml). The product precipitated at −15° C. is filtered and dried giving 24.5 g (83%) of 1,3-didecanoyl-2-docosanoyl glycerol.

EXAMPLE III

1-O-Benzyl-3-octanoyl-sn-glycerol

Caprylic anhydride (2.74 mmole, 0.928 g) and Lipozyme (1 g) are added to a mixture of 1-O-benzyl-sn-glycerol (3.43 mmole, 0.500 g) in methylene chloride (50 ml) and stirred overnight at room temperature. The enzyme is filtered and the solution is treated with ion exchange resin IR-400 (OH⁻) to remove remaining octanoic acid. The evaporation of the solvent gives the product which, if necessary, can be further purified on silica column using a mixture of hexane, ethyl ether, acetic acid (50:50:1) as the eluent. Yield of the product is 0.6 g (71%).

EXAMPLE IV

1-Octanoyl-3-lysophosphatidycholine

Caprylic anhydride (29 mmole, 7.8 g) and Lipozyme (6 g) are added to a mixture of L-α-glycerophosphorylcholine (7.7 mmole, 2.0 g) in methylene chloride (30 ml). The acylation is complete in 6 hours and enzyme is filtered. The filtrate is diluted with methanol (100 ml), treated with IRA-400(OH-) to remove octanoic acid and evaporated to give 2.1 g (71%) of the product.

EXAMPLE V

D-glucopyranosyl-(1→3)-(1-octanoyl-sn-glycerol)

A mixture of 6-O-tert-butyldiphenylsilyl-D-glycopyranosyl-(1->3)-sn-glycerol (7.3 mmole, 3.5 g), palmitic acid anhydride (8.5 mmole, 4.21 g) and Lipozyme (12 g) in methylene chloride (250 ml) is stirred at room temperature for 20 hours. After 20 hours enzyme is filtered, the filtrate is cooled to 0° C. to precipitate unreacted anhydride and palmitic acid which are subsequently removed by filtration. The remaining anhydride and acid can be removed with IRA-400(OH-) Further (optional) purification on the silica column with chloroform methanol 9:1 provides 2.0 g (56%) of the product.

EXAMPLE VI

4-(Di-isopropylidene)phosphinyl-1-myristoyloxy-2-hydroxybutane

A mixture of 4-(di-isopropylidene)phosphinyl-1,2-dihydroxybutane (25 mmole, 5 g), myristic acid anhydride (50 mmole, 22 g), Lipozyme (20 g) in methylene chloride (500 ml) are stirred 2 hours at room temperature. The enzyme is removed by filtration, excess of anhydride and myristic acid were removed with anion exchange resin IRA-400(OH⁻). Evaporation gives 6.0 g (52%) of the product.

What is claimed is:

1. A process for preparing 1,3 diacylglycerides comprising: mixing a catalytic amount of 1,3-specific lipase enzyme with a mixture of from 20% to 60% of a water immiscible hydrocarbon or chlorinated hydrocarbon, from 3% to 40% glycerol, and from 3% to 40% fatty acid anhydride for at least one hour at a temperature of from about 20° C. to about 5° C. to form the 1,3-diacylglyceride; and separating the 1,3 diacylglyceride.

2. A process according to claim 1 wherein the mixture comprises from 10% to 25% fatty acid anhydride, 10% to 25% glycerol and 50% to 60% hydrocarbon.

3. A process according to claim 2 wherein said enzyme is immobilized on a resin or absorbed on a support.

4. A process according to claim 3 wherein said chlorinated hydrocarbon is methylene chloride.

5. A process according to claim 4 wherein said fatty acid anhydride consist of saturated or unsaturated fatty acids having from 8 to 24 carbon atoms.

6. A process according to claim 5 wherein said fatty acid anhydride is derived from oils selected from the group consisting of partially hydrogenated and unhydrogenated sunflower seed oil, soybean oil, canola, rapeseed oil, safflower oil, marine oils, corn oil and mixtures thereof.

7. A process according to claim 5 wherein said fatty acid anhydride is selected from the group consisting of anhydrides of octanoic acid, decanoic acid, lauric acid, myristic acid, stearic acid, palmitic acid and oleic acid.

8. A process for preparing a 1-acyl-3-substituted diglyceride comprising: mixing a catalytic amount of a 1,3 specific lipase enzyme with
    (a) from about 3% to about 40% of a glycerol derivative,
    (b) from about 3% to about 40% of a fatty acid anhydride, and
    (c) from about 20% to about 60% of a water-immiscible hydrocarbon or halogenated hydrocarbon solvent for at least one hour at a temperature of at least 20° C. and thereafter isolating the 1-acyl-3-substituted glycerol.

9. A process according to claim 8 wherein the mixture comprises from 10% to 25% fatty acid anhydride, 10% to 25% glycerol derivative and 50% to 60% hydrocarbon.

10. A process according to claim 9 wherein said enzyme is immobilized on a resin or absorbed on a support.

11. A process according to claim 10 wherein said halogenated hydrocarbon is methylene chloride.

12. A process according to claim 11 wherein said fatty acid anhydride consist of saturated or unsaturated fatty acids having from 8 to 24 carbon atoms.

13. A process according to claim 12 wherein said fatty acid anhydride is selected from the group consisting of anhydrides of octanoic acid, decanoic acid, lauric acid, stearic acid, myristic acid, palmitic acid, or oleic acid.

14. A process according to claim 8 wherein said glycerol derivative is selected from the group consisting of alkyl ethers, phosphates, phospholipids, sugars, alkyl phosphates, phosphonates and sugar glycosides.

15. A process according to claim 14 wherein said alkyl ethers have from 1 to 18 carbon atoms.

16. A process according to claim 14 wherein the sugar glycoside is selected from the group consisting of glucose, fructose, maltose, sucrose, and tri- or tetrapolysaccharides.

17. A process according to claim 14 wherein said phospholipid is phosphocholine.

18. A process according to claim 14 wherein said alkyl phosphate is a dialkyl phosphate wherein each alkyl group has 1 to 22 carbon atoms.

* * * * *

UNITED STATES PATENT AND TRADEMARK OFFICE
CERTIFICATE OF CORRECTION

PATENT NO.   : 5,137,660
DATED        : August 11, 1992
INVENTOR(S)  : A. W. Mazur et al.

It is certified that error appears in the above-identified patent and that said Letters Patent is hereby corrected as shown below:

Column 7, line 59, $5^{\circ}C$ should be $50^{\circ}C$

Signed and Sealed this

Thirty-first Day of August, 1993

Attest:

BRUCE LEHMAN

Attesting Officer

Commissioner of Patents and Trademarks